United States Patent
Bieberich (10) Patent No.: US 6,764,502 B2
(45) Date of Patent: Jul. 20, 2004

(54) HIGH-EFFICIENCY COOLING PADS, MATTRESSES, AND SLEEVES

(75) Inventor: Mark Thomas Bieberich, Edina, MN (US)

(73) Assignee: Arizant Healthcare Inc., Eden Prairie, MN (US)

(*) Notice: Subject to any disclaimer, the term of this patent is extended or adjusted under 35 U.S.C. 154(b) by 16 days.

(21) Appl. No.: 10/036,044

(22) Filed: Dec. 28, 2001

(65) Prior Publication Data

US 2002/0058975 A1 May 16, 2002

Related U.S. Application Data

(63) Continuation of application No. 09/460,478, filed on Dec. 14, 1999, now Pat. No. 6,402,775.

(51) Int. Cl.$^7$ ................................................ A61F 7/00
(52) U.S. Cl. ......................... 607/104; 607/107; 607/108
(58) Field of Search ................................ 607/104, 107, 607/108; 601/16, 17; 5/644, 651.2, 655.9, 422, 680

(56) References Cited

U.S. PATENT DOCUMENTS

| | | | | |
|---|---|---|---|---|
| 3,757,366 A | * | 9/1973 | Sacher | 607/107 |
| 3,867,939 A | * | 2/1975 | Moore et al. | 607/104 |
| 4,107,509 A | * | 8/1978 | Scher et al. | 219/211 |
| 4,233,700 A | * | 11/1980 | Spann | 5/652.1 |
| 4,768,250 A | * | 9/1988 | Kato | 5/689 |
| 4,844,072 A | * | 7/1989 | French et al. | 607/104 |
| 5,226,188 A | * | 7/1993 | Liou | 5/652.1 |
| 5,626,386 A | * | 5/1997 | Lush | 297/180.13 |
| 5,964,723 A | * | 10/1999 | Augustine | 602/42 |
| 5,986,163 A | * | 11/1999 | Augustine | 602/42 |
| 5,991,948 A | * | 11/1999 | Stanley et al. | 5/709 |
| 6,085,369 A | * | 7/2000 | Feher | 5/423 |
| 6,119,474 A | * | 9/2000 | Augustine et al. | 607/107 |
| 6,245,094 B1 | * | 6/2001 | Pompei | 607/104 |

* cited by examiner

Primary Examiner—Beverly M. Flanagan
(74) Attorney, Agent, or Firm—Incaplaw; Terrance A. Meador

(57) ABSTRACT

Cooling pads, mattresses, and limb-conforming sleeves reduce a person's temperature by evaporative and/or conductive cooling. An open cell foam pad defines an internal air flow passages proceeding according to serpentine or other desired routing. The pad is wetted, and a blower circulates air through the air flow passage and evaporatively cools the pad by removing warm water vapor. By contacting the cooled structure, the person is conductively cooled. The pad also employs evaporative cooling if water is permitted to seep from the foam pad onto the person's skin and subsequently evaporate. Another cooling device is a multilayer evaporative cooling mattress. The mattress comprises an open cell foam structure having a person-receiving side and a base side. At the person-receiving side lies an absorbent layer with internal liquid delivery lines, and optionally having an outer film applied thereto. Beneath the absorbent layer is an air manifold comprising air flow passages defined in a cushion layer, or an open mesh layer interposed between the absorbent layer and cushion layer. Another cooling device is a thermal cooling sleeve, with a series of multiple elongated, parallel ridges. Pairs of adjacent ridges are separated by intervening channels, and each ridge has a lateral liquid passage through it. When the first and last ridges are brought around to meet each other, the ridges form a contiguous sleeve. Within the sleeve's body, the passages cooperatively define a continuous conduit proceeding from ridge to ridge inside the sleeve.

18 Claims, 4 Drawing Sheets

HIGH-EFFICIENCY COOLING PADS, MATTRESSES, AND SLEEVES

This is a continuation application of U.S. patent application Ser. No. 09/460,478, filed on Dec. 14, 1999 U.S. Pat. No. 4,402,775.

BACKGROUND OF THE INVENTION

1. Field of the Invention

The present invention relates to devices that utilize evaporative, convective and/or conductive cooling to cool the human body in aid of surgery, medical treatment, therapy, or comfort. Some exemplary cooling structures include various configurations of thermal cooling devices.

2. Description of the Related Art

Temperature control in humans has important medical consequences. In order to maintain optimum health, the human body must maintain a core temperature within a very narrow range. Core body temperature changes as small as 0.1° Celsius trigger thermoregulatory responses such as vasoconstriction, vasodilation, shivering, or sweating. A narrow temperature range is optimal for human cellular functions, biochemical reactions, and enzymatic reactions. Outside this range of temperatures, the human body experiences hypothermia (excessive cold) or hyperthermia (excessive hot).

Hyperthermia can result from illness or environmental heat stress, among other causes. In some cases, healthy people suffer hyperthermia when their natural cooling mechanisms, such as sweating, are overwhelmed during heavy physical work in a hot environment. This situation can become even worse if the person fails to drink enough fluids, and therefore cannot sweat adequately. Heat stress disorders, categorized in ascending order of severity, include: heat cramps, heat syncope, heat exhaustion, and heat stroke. Normally, discomfort causes people choose to stop working before the onset of heat exhaustion, but competitive athletics or military activities sometimes push people beyond the limits of health.

Hyperthermia can also result from fever associated with illness. Fever may arise from infection, tumor necrosis, thyroid storm, malignant hyperthermia, brain injury, and other causes. Brain injuries that cause hyperthermia usually involve the hypothalamus, and may be caused by tumors, stroke, head injury, or cardiac arrest (in the case of ischemic brain injury).

Some consequences of hyperthermia include fluid and electrolyte imbalances, increased cellular metabolic rates, and cognitive impairment. More serious consequences include motor skill impairment, loss of consciousness, and seizures. Ultimately, hyperthermia can cause irreversible cellular injury (especially of the highly metabolic brain and liver cells), organ failure, and death. Hyperthermia is a condition that, depending on its severity, may require immediate cooling treatment to return the person's core temperature to normal.

Cooling treatment may also have other important uses. In some situations, mild or moderate hypothermia is believed to provide beneficial protection against injury. Moreover, induced hypothermia can be beneficial when the blood flow to some or all of the brain has been interrupted. Brain ischemia due to an interruption of blood flow may occur during cardiac arrest, surgery on the blood vessels of the brain, stroke, traumatic brain injury, or open heart surgery. Cooling the brain before (or in some cases after) these events can protect the brain from injury, or at least decrease the severity of the ultimate brain damage.

Physicians have used various devices and techniques to cool the human body, including pharmacological cooling and various types of mechanically induced cooling. Mechanically induced cooling approaches generally fall into one of these categories: conductive, convective, or evaporative. While different implementations have been tried, many are limited by lack of practicality, difficulty of use, ineffectiveness, and/or excessive power consumption.

One example of conductive cooling involves packing a hyperthermia person's body in ice, or immersing the person in cool or cold water. While ice is an effective cooling agent, it is painful to the person, potentially damaging to the skin, difficult to obtain in large quantities, and impractical for long term use. Water baths can be effective, although they are not practical for the comatose or intensive care patient, or for long term use. In one less effective, but common method of conductive cooling, a person may be placed in contact with a cold-water-circulating mattress and/or cover. Water inside the mattress removes heat from the person by conduction wherever the surface of the mattress thermally contacts the person's skin. Although there is some benefit to such devices, they are often uncomfortable and heavy, and provide inefficient thermal contact because they are not precisely shaped to the body.

In contrast to conductive cooling, convective cooling involves blowing air onto a person. Convective cooling is the least effective method of cooling from a thermodynamic point of view. Room temperature air can be blown very inexpensively with a fan. However, its cooling effectiveness is severely limited due to the thermal capacity of air, and related heat transfer coefficients.

For more efficient convective cooling, the air can be cooled before being blown onto the person. Air can be cooled, for example, with a traditional compression or heat-pump air conditioner, vortex cooling, or with thermoelectric cooling. Cooled air can also be generated using the "swamp cooler" principle of vaporizing water into the air stream. When water evaporates into the air, it cools the air. Then, the cooled air is applied to a person.

After the air is cooled with one of the foregoing techniques, it can be delivered to a person by cooling the air in the person's room. To save energy, cooling can be confined to the person rather than the whole environment surrounding the person. One technique that uses this approach is the convective thermal device, which has been implemented in a variety of forms.

Although convective cooling removes the stress of environmental heat, it is minimally effective in active cooling. This limited thermodynamic effectiveness is particularly evident when trying to cool people with fevers. Generally, in order to be cooled by convection, a feverish person must be anesthetized and paralyzed to prevent the body's heat-producing shivering response. Further, due to the thermodynamic inefficiency of convective cooling, this method of cooling uses considerable electrical power and generates considerable waste heat, which can be a problem in emergency rooms or intensive care units.

Having discussed conductive and convective cooling, the final mechanically induced cooling mechanism is evaporative cooling. Sweating is a principal example of evaporative cooling. Because water has a large heat of vaporization, large amounts of heat can be removed from the body by evaporating relatively small amounts of water. For example, when a gram of water evaporates, it extracts 540 calories of heat (2.26 kJ) from the skin. On hot summer days, many people practice basic evaporative cooling by wetting their skin or clothing with water, and permitting the water evaporate. Medical staff employ evaporative cooling by giving sponge baths to patients, where the unclothed patient is wetted with water and allowed to dry by evaporation. Sometimes a fan is pointed at the person to increase the evaporation rate. While sponge baths are indeed effective, they are labor intensive, messy, demeaning to body-conscious people, and impractical for prolonged cooling. Finally, evaporative cooing has limited effectiveness in high humidity environments.

Therefore, as shown above, conductive, convective, and evaporative cooling systems each have certain benefits and limitations. And, although some of the foregoing cooling products have certain advantages and might even enjoy some commercial success, engineers at Augustine Medical, Inc. are continually seeking to improve the performance and efficiency of human cooling systems. Some areas of possible focus include simplifying hardware designs, boosting the effectiveness of cooling systems, and cooling specific body parts.

An additional area of focus concerns the management of the liquid source during evaporative cooling. Introducing too much liquid causes liquid to spill over the area of focused cooling (the "cooling field"), and pool under the person. Pooling of contaminated liquids presents hygienic and esthetic problems in the medical environment. On the other hand, if too little liquid is supplied, the cooling field may dry out and stop or reduce cooling effectiveness.

SUMMARY OF THE INVENTION

Broadly, the present invention introduces a number of improved cooling devices that utilize evaporative and/or conductive cooling to reduce a person's temperature in aid of surgery, medical treatment, therapy, or comfort. Some exemplary cooling structures include thermal cooling mattresses, pads, and limb-conforming sleeves.

One embodiment of the invention involves thermal cooling pads or mattresses that are placed beneath a person, and cool by conduction (and optionally evaporation, as well). According to one such embodiment, a cooling pad is embodied by a foam structure such as an open cell foam pillow or mattress. The pad defines an internal air flow passage proceeding from an air inlet to an air outlet according to a desired routing, such as a serpentine path. The pad may include various recesses shaped to receive certain body parts. The pad is wetted with an evaporation liquid, such as water. Wetting may be conducted by hand, or by routing the liquid through an internal liquid flow passage. When an air blower is coupled to the air inlet, air circulates through the air flow passage, and evaporatively cools the pad by removing warmed water vapor. Through contact with the cooled structure, the person is therefore cooled by conduction. And, depending upon whether the foam pad is covered with a sealant or not, the pad may also employ evaporative cooling if water is permitted to seep from the foam pad onto the person's skin and subsequently evaporate.

Another type of cooling pad is a multi-layer evaporative cooling mattress. The mattress comprises an open cell foam structure having a person-receiving side and a base side. An air manifold abuts the base side. The air manifold may comprise one or more passages defined in the foam mattress, or an open mesh layer. Above the air manifold is an absorbent layer with internal liquid delivery lines. An outer film is applied to the absorbent layer.

In contrast to the cooling mattresses and pads, a different embodiment of the invention concerns a cooling sleeve. Such a device is constructed using an open cell foam structure that is configured to provide a series of multiple elongated, parallel ridges of triangular or trapezoidal cross-section. Each pair of adjacent ridges is separated by an intervening channel, and each ridge has a lateral air flow passage through it. When the first and last ridges are brought around to meet each other, the ridges form a contiguous sleeve. Within the body of the sleeve, the air flow passages cooperatively define a continuous conduit proceeding from ridge to ridge inside the sleeve. The ridges may be interconnected, or they may be separately attached to a common base layer.

Accordingly, as discussed above, the invention may be implemented to provide various types of apparatus, such as cooling mattresses, pads, and sleeves. In contrast, certain other embodiments concern methods for utilizing such cooling equipment.

The invention affords its users with a number of distinct advantages. By using a blower to induce evaporative cooling, the invention avoids the need for power consuming refrigeration equipment. As another advantage, evaporative cooling is thermally self-limiting, because it will not produce surface temperatures that would freeze skin, as is the case with ice packs. Also, unlike ice and other phase change materials that can only maintain fixed temperatures for a limited time, cooling with this invention can be sustained indefinitely by periodically adding water to the cooling field.

As another advantage, the use of materials such as open cell foam enables the cooling devices of this invention to readily conform to the person's body and thereby boost cooling effectiveness. This provides a marked improvement over prior approaches that practice cooling by placing an inflatable, water-filled mattress under the body. Inflatable, water-filled mattresses can only cool those body parts that support the reclining body and therefore contact the mattress. These body parts include the head, shoulder blades, buttocks, and various locations on the legs.

As another advantage, absent from previous approaches, this invention may incorporate a super-absorbent material into thermal cooling mattresses or pads. The super-absorbent material is capable of holding a large volume of water relative to its mass. This material, once wetted, can provide hours of evaporative cooling without the need for a liquid reservoir and piping system to replenish the cooling field. Consequently, cooling devices equipped with super-absorbent material discourage the introduction of too much cooling liquid, and help prevent the cooling liquid from overwhelming the cooling field and spilling over.

The invention also provides a number of other advantages and benefits, which should be apparent from the following description of the invention.

DETAILED DESCRIPTION

The nature, objectives, and advantages of the invention will become more apparent to those skilled in the art after considering the following detailed description in connection with the accompanying drawings.

Hardware Components & Interconnections

Introduction

One aspect of the invention concerns a cooling device, which may be implemented in a number of different forms as discussed below. This equipment is used to cool the human body in aid of surgery, medical treatment, therapy, or comfort. The invention utilizes evaporative and/or conductive cooling. Evaporative cooling involves applying a liquid to bodily regions and permitting evaporation to occur naturally or actively encouraging evaporation by directing an evaporating gas to the wetted bodily regions. With conductive cooling, the cooling structure itself is cooled by some means such as evaporation. Since the cooling structure contacts the person, the person is ultimately cooled as well. Some exemplary cooling devices include thermal pads, mattresses, and limb-conforming cooling sleeves.

Thermal Cooling Pad

Figure 1A:
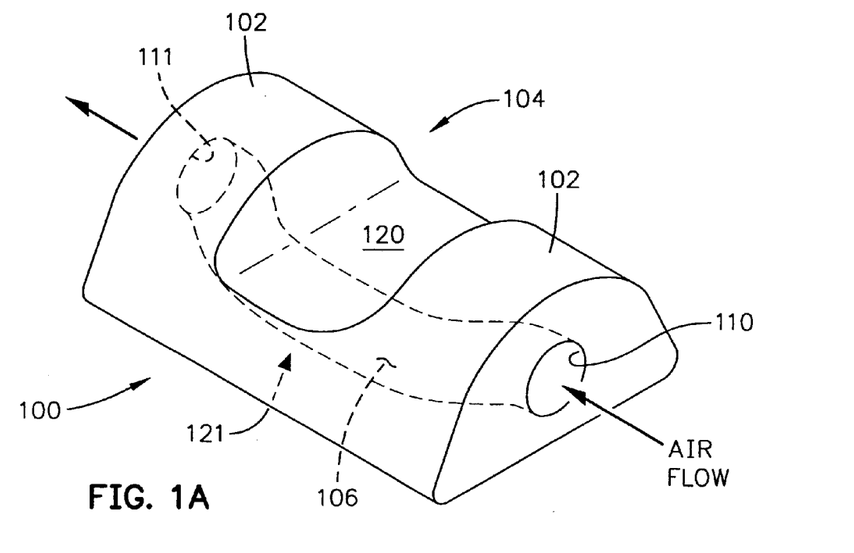
FIG. 1A is a perspective view of a thermal cooling pad comprising an open cell foam structure employing an internal air flow passage according to the invention.

FIG. 1A shows one example of thermal cooling pad 100, in the form of a pillow. The pad 100 comprises a material that readily absorbs water and is amenable to evaporative cooling when air flows as described below. To illustrate some examples, this water absorbent material may comprise open cell foam, natural or synthetic sponge, "super-absorbent material," etc. So-called "super-absorbent" materials are substances capable of absorbing significantly more water than their own mass and volume, and one example is starch-grafted sodium polyacrylate (SAP), which is present in some types of diapers. SAP material may be processed into a fibrous, cotton-like form and woven into a sheet of gauze-like material.

SAP material can absorb more than twice its volume and four-hundred times its mass in water. Thirty grams of SAP (less than the amount in a typical disposable diaper) can absorb approximately 1,000 grams of water. The evaporation of 1,000 grams of water removes 2,400 kilojoules of heat. If a typical seventy kilogram human has a specific heat near the specific heat of water, it would only take 1,470 kilojoules to reduce the mean body temperature by five degrees Celsius. Thus, as discovered by the present inventor(s), and illustrated by the foregoing example, water held by a super-absorbent layer can provide a significant amount of body cooling. The duration of cooling is significant, as well. Namely, while sleeping, the body metabolically generates about one hundred Watts of heat. This heat generation would be canceled by the evaporation of about 1,000 grams of water per hour, neglecting other thermal loads on the system. At this rate, one liter of water would provide about six hours of cooling.

Referring to FIG. 1, the pad 100 defines an internal air flow passage 106 proceeding from an air inlet 110 to an air outlet 111. The passage 106 may assume a straight, serpentine, lattice, or other path shape designed to maximize the exposure of air in the passage to the foam structure, and thereby maximize evaporative cooling of the water-saturated foam. As another example, there may be multiple, separate air flow passages in parallel. Different variations of multiple/single air flow passage(s), inlet(s), and outlet(s) may be use used to best suit the particular application at hand.

The pad 100 may also define an internal liquid flow passage (not shown) for the purpose of admitting water or another evaporative cooling liquid into the pad. Although the liquid flow passage may assume any desired shape, serpentine or other paths that thoroughly traverse the pad 100 are especially effective in saturating all areas of the pad 100. As another example, multiple liquid flow passages (whether interconnected or not) may be used in parallel with each other to increase liquid flow or saturation effectiveness. The liquid flow passage(s) may include a water outlet, but this is unnecessary because the intent of the liquid flow passage is to saturate the pad 100 rather than transport liquid through the pad. The liquid flow passage may comprise a void that is cut or otherwise defined from the foam material. As an alternative or additional feature, the pad 100 may include a perforated tube (not shown) that resides in the liquid flow passage, and distributes water through the perforations, in drip irrigation fashion. Alternatively, the liquid flow passage(s) may be omitted if the pad 100 is soaked in water prior to use, or manually irrigated with a cup, irrigation line, or faucet, etc. In fact, if the pad has a relatively small size, the pad 100 may be capable of achieving sufficiently thorough water saturation through exclusively external, manual irrigation.

The foam material of the pad 100 preferably includes a sufficient density to support the intended body parts without collapsing the internal air flow passage(s). If desired, multiple layers of foam may be used, where softer foam is used for surfaces that contact the patient, and stiffer foam is used to maintain the internal passages.

The pad 100 includes a person-receiving upper surface 120, and an opposite, bottom surface 121. If desired, the bottom surface 121 may be coated, adhered, or temporarily covered with a layer of sealant to prevent moisture from wetting bedding, pillows, or other materials beneath the pad 100 during use. Depending upon the particular application, the person-receiving surface 120 may also be coated, adhered, or temporarily covered with a sealant to prevent the pad 100 from wetting the person. The foregoing sealant layers may be permanently applied to the foam structure, for example, by chemical or heat curing. Alternatively, removable sealant may be used, such as a roll of plastic film or tailored cover that is removed after each use. Applying sealant to the surface 120 forestalls any cooling of the person by evaporation since the person's skin does not get wet. Nonetheless, the person is still cooled by conduction. Namely, when air runs through the water-laden pad, the pad itself experiences evaporative cooling; in turn, the cooled pad conductively cools the person's body parts that thermally contact the pad. For this reason, any sealant placed on the person-receiving surface 120 is preferably thermally conductive.

Figure 1B:
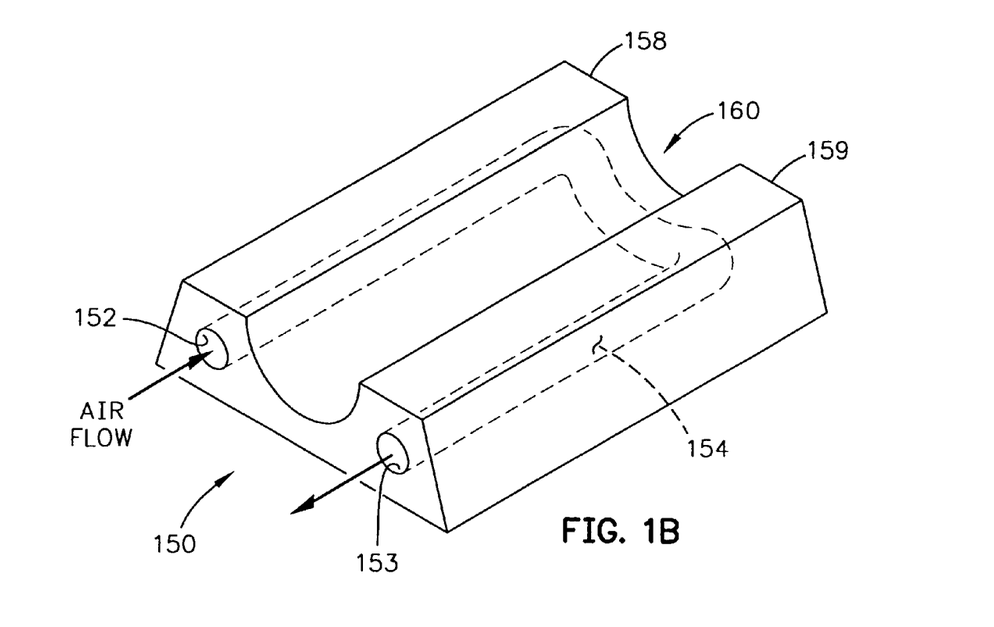
FIG. 1B is a perspective view of a thermal cooling pad shaped to accommodate a person's limb, according to the invention.

The pad 100 may also be cut, molded, or otherwise formed to define shapes that help receive, prop, or position body parts. As illustrated, the pad 100 includes a recess 104 with adjoining ridges 102 to hold a person's head and neck in place. FIG. 1B shows a different example 150, which is shaped to accommodate a limb. This device 150 is cut, molded, or otherwise shaped to form an elongated channel 160 that defines a pair of parallel, outlying ridges 158–159. Dimensions of the channel 160 may be selected to accommodate a desired shape and size of arm, forearm, leg, etc. The structure 150 internally defines a "U-shaped" air flow passage 154, with an inlet 152 and outlet 153. Other air flow paths, (e.g. serpentine) are contemplated as well.

Thermal Cooling Mattress

Figure 2:
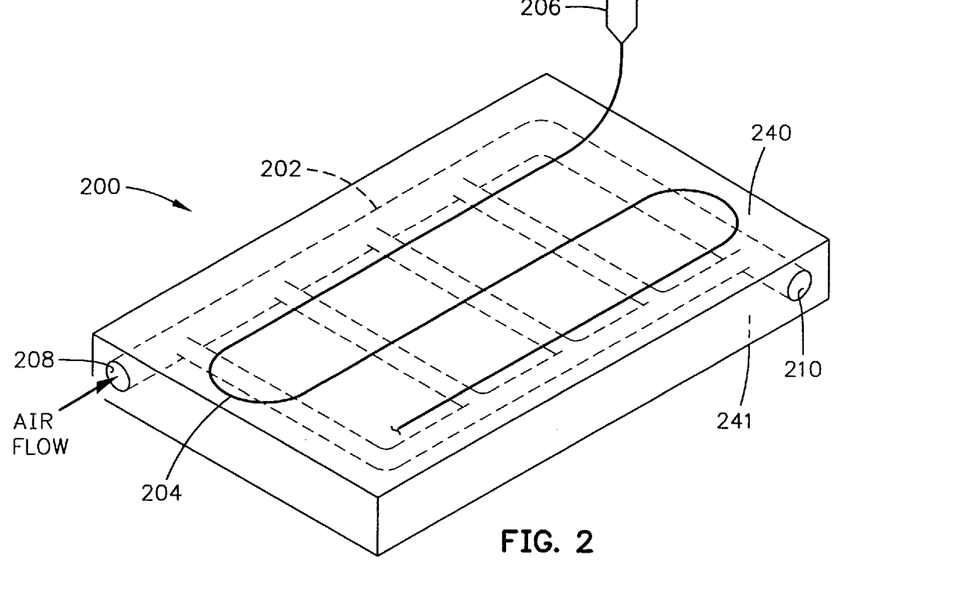
FIG. 2 is a perspective view of a thermal cooling mattress according to the invention.

In addition to the cooling pads discussed above, the invention also includes various cooling mattresses. FIG. 2 shows one example embodied by the cooling mattress 200. Like the pad 100, the mattress 200 cools itself by receiving and then evaporating water or some other evaporative medium. Then, through conduction, the cooled mattress cools the person's body parts that thermally contact the mattress.

The mattress 200 comprises open cell foam or other material similar to the pad 100, although the mattress 200 may be substantially larger so as to accommodate a reclining person. The mattress may be cut, molded, or otherwise formed to define shapes that help receive, prop, or position body parts. The mattress 200 includes a person-receiving upper surface 240 and an opposite, bottom surface 241.

Also resembling the pad 100, the mattress 200 includes at least one internal air flow passage 202 proceeding from an air inlet 208 to an air outlet 210. Different variations of multiple/single air flow passage(s), inlet(s), and outlet(s) may be used to best suit the particular application at hand. The mattress 200 also defines an internal liquid flow passage 204 to admit water or another volatile cooling liquid into the mattress 200. Although the liquid flow passage 202 may assume any desired shape, serpentine or other paths that thoroughly traverse the mattress 200 are especially effective in saturating all areas of the mattress 200. The liquid flow passage 202 may also include a perforated tube that resides in the passage and distributes water through the perforations, in drip irrigation fashion. Alternatively, the mattress 200 may be soaked in water prior to use, or manually irrigated with a cup, irrigation line, or faucet, etc. In the illustrated embodiment, the mattress 200 receives evaporative cooling liquid from a water source 206.

Figure 3:
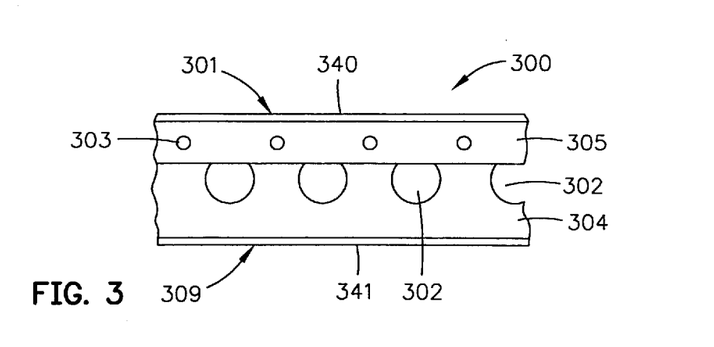
FIG. 3 is a partial cross-sectional side view of one type of multi-layer thermal cooling mattress according to the invention.
Figure 4:
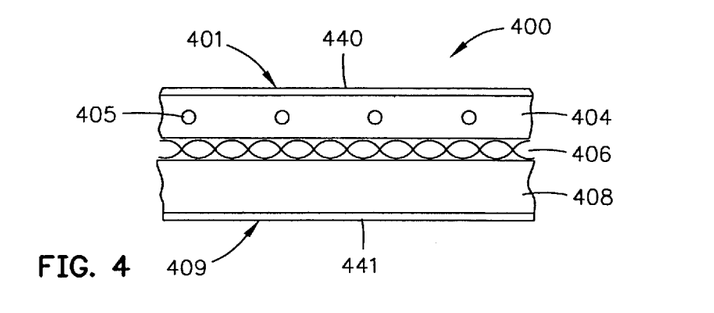
FIG. 4 is a partial cross-sectional side view of a different type of multi-layer thermal cooling mattress according to the invention.

The mattress 200 may be enhanced with various internal layers, as shown by the mattress sections depicted in FIGS. 3–4. The mattress section 300 (FIG. 3) has a person-receiving surface 340 and an opposite, bottom surface 341. Between the surfaces 340–341 lies a cushion layer 304 of absorbent material, such as open cell foam, natural or synthetic sponge, etc. The cushion layer 304 provides the chief structure of the mattress, and thus establishes the desired level of firmness of the mattress 200. The cushion layer 304 internally defines an air manifold 302, which is embodied by various interconnected air flow passages defined in the layer 304. Above the layer 304 lies an absorbent layer 305, comprising a material with sufficient liquid absorbency for use as an evaporative cooling layer. As an example, the layer 305 may have more softness than the layer 304 (to better cushion the person's body), and also have more absorbency than the layer 304 (to better retain water received from the liquid flow passages 303). As an example, the absorbent layer 305 may comprise a super-absorbent material. The absorbent layer 305 houses one or more liquid flow passages 303 to distribute water or another evaporative cooling liquid throughout the layer 305.

One or both of the surfaces 340, 341 may be coated, adhered, temporarily covered by, or otherwise topped with corresponding sealant layers 301, 309, such as plastic or another water impenetrable substance. The sealant layer 309 prevents moisture in the mattress from wetting bedding, pillows, or other materials beneath the mattress 300 during use. The sealant layer 301 prevents the mattress from wetting the person. The sealant layer 301 forestalls any evaporative cooling of the person since the person's skin does not get wet. Nonetheless, the person is still cooled by conduction. Namely, when air runs through the water-laden mattress 300, the mattress 300 itself experiences evaporative cooling; in turn, the cooled mattress conductively cools the person's body parts that thermally contact the mattress. For this reason, any sealant placed on the person-receiving surface 340 may comprise a thermally conductive material, or a material with sufficient thinness to avoid acting like a thermal insulator.

As an alternative to the arrangement of FIG. 3, a different mattress 400 may be constructed as shown by FIG. 4. The mattress 400 includes a person-receiving surface 440 and an opposite, bottom surface 441. Between these surfaces, the mattress 400 includes similar layers as in the mattress 300, including a sealant layers 401, absorbent layer 404 (with liquid flow passages 405), cushion layer 408, and sealant layer 409. Unlike the mattress 300, however, the mattress 400 includes an air manifold 406 that is separate from the cushion layer 408, instead of being internally defined by voids in the layer 408. The air manifold 406 comprises a series of parallel tubes, open mesh, fibrous mat, layer of coil springs, or another suitably air permeable structure.

Limb-conforming Cooling Sleeve

In contrast to the previously described thermal cooling pads and mattresses, typically used by placing under a reclining person, a different embodiment of the invention concerns a selectively activated thermal cooling sleeve. This device is laid open to accept a person's limb, then closed to form a limb-supporting sleeve. Generally, this device comprises a block of open cell foam with a series of parallel, elongated channels removed, thereby defining a series of parallel ridges with trapezoidal or triangular cross-section. When the outermost ridges are brought together, all ridges snug together in the spaces formerly occupied by the channels, and the ridges cooperatively form a contiguous limb-supporting sleeve.

Figure 5:
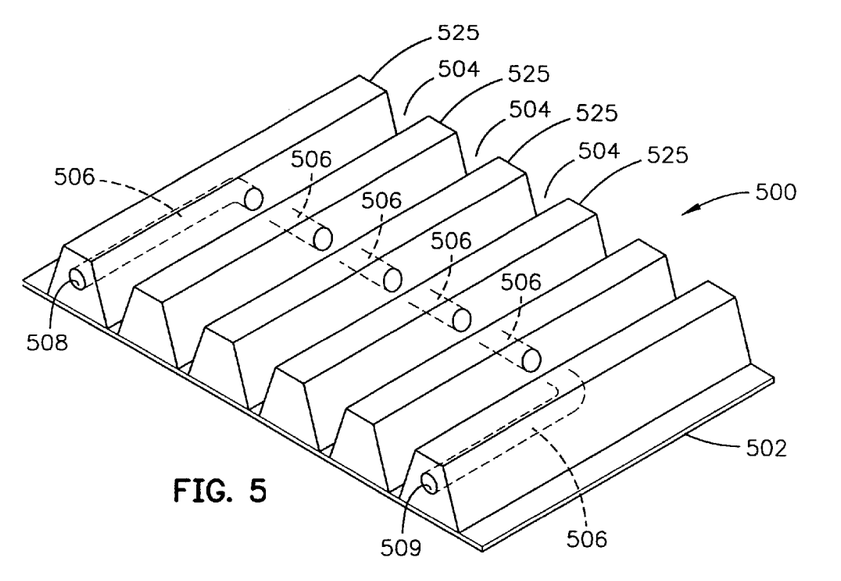
FIG. 5 is a perspective view of a limb support cooling structure according to the invention, shown in relaxed state.
Figure 6:
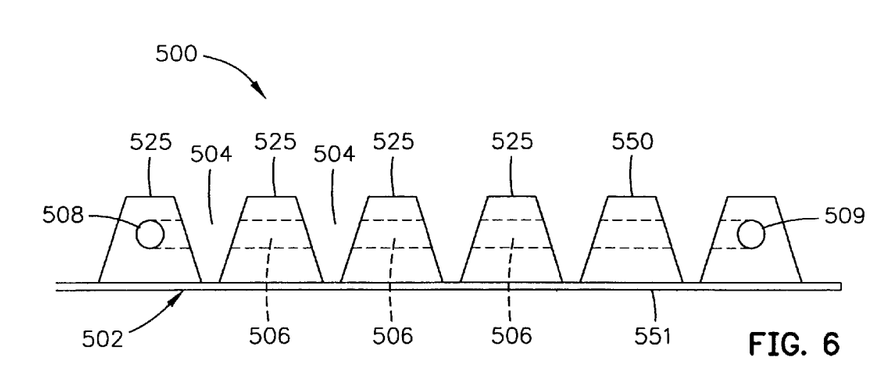
FIG. 6 is a side view of the limb support cooling structure of FIG. 5.
Figure 7:
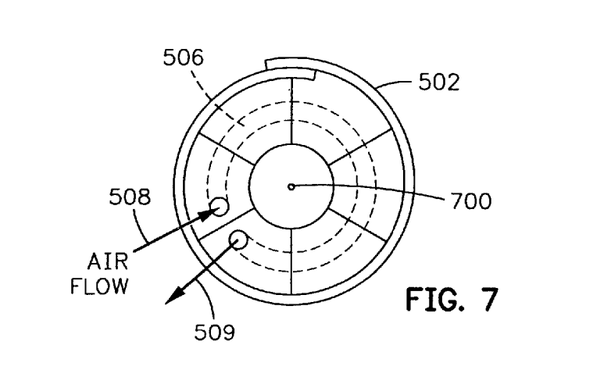
FIG. 7 is a side view of the limb support cooling structure of FIGS. 5–6, shown in wrapped position.

FIGS. 5–7 show an exemplary cooling sleeve 500 in greater detail. The sleeve 500 comprises a structure of open cell foam, synthetic or natural sponge, or other suitable water-absorbent material. The sleeve 500 has a person-receiving surface 550 and an opposite, bottom surface 551. The person-receiving surface 550 may be temporarily or permanently covered or coated by a moisture barrier such as plastic or another sealant to prevent water leakage from the absorbent sleeve onto the person.

The sleeve 500 is cut, molded, or otherwise shaped to define multiple elongated channels 504. Each channel 504 defines a pair of outlying ridges or "blocks" 525 of the foam structure. Thus, the sleeve 500 includes a series of parallel ridges 525. In the illustrated example, the ridges 525 have a trapezoidal lateral cross-section as best seen in FIG. 6. Alternatively, the ridges may have triangular or other cross-sectional shapes that are narrower toward the person-receiving surface 550 and wider at the bottom surface 551.

The structure 500 may comprise a single, unitary piece. In this case, a wrap layer 502 constitutes a lower layer of foam integral to all ridges 525. In another embodiment, the ridges 525 are physically distinct from each other, and a separate wrap layer 502 is added to provide a common mounting surface for all ridges.

Each ridge has an internal air flow passage 506. The outermost ridges include an inlet 508 and outlet 509, which are connected to their respective internal air flow passages 506. Thus, the ridges 525 and air flow passages 506 are configured such that, when the outermost ridges are brought around to meet each other (FIG. 7), the ridges 525 form a contiguous sleeve having a body and a hollow, limb-receiving core 700. In this arrangement, the air flow passages 506 cooperatively define a continuous conduit proceeding from ridge to ridge inside the sleeve body.

Operation

Figure 8:
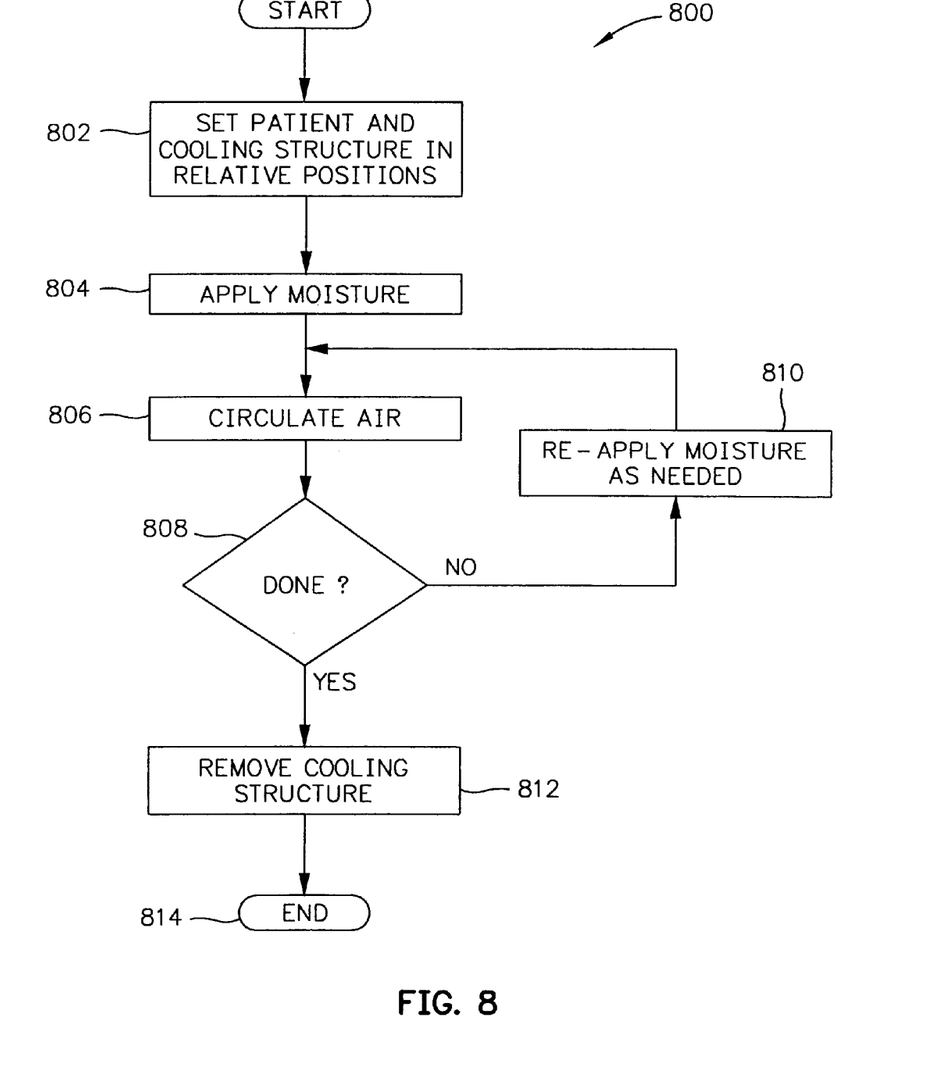
FIG. 8 is a flowchart of an operational sequence for using the cooling systems of FIGS. 1A–7.

In addition to the various cooling devices described above, a different aspect of the invention concerns appropriate methods for operating such equipment. FIG. 8 depicts a sequence 800 for operating a thermal cooling pad, mattress, or selectively configurable limb sleeve. These steps 800 may be performed by various people, depending upon the environment where the cooling device is used. For example, the steps 800 may be performed by the subject or a family member at home, by attendants at a nursing facility, medical staff at a hospital, therapists at a treatment center, etc.

For ease of explanation, but without any intended limitation, the example of FIG. 8 is described primarily in the context of the cooling pad 100 of FIG. 1A. In step 802, the person and/or pad 100 are positioned for operation of the pad 100. For greatest cooling, the person should be unclothed, or at least those body parts in contact with the pad. The pad 100 is placed on the person's bed, and the person lies in bed with his/her head in the recess 104. In the case of the mattress 200, an operator positions the mattress 200 on a suitable surface and the person reclines atop the mattress 200. In the case of the limb support sleeve 500, the operator positions the person's treating limb upon one of the ridges 525, and wraps the ridges around the limb to form a circle, such that adjacent ridges come together. Thus, the outermost ridges meet each other, and the all ridges collectively form the contiguous sleeve of FIG. 7 with the person's limb inside the core 700.

After positioning the person and/or cooling device in step 802, medical staff moisten the cooling pad in step 804. The pad may be moistened with water or another wetting agent that is suitably prone to evaporation, hypoallergenic, safe, effective in cooling, nonflammable, etc. An antibacterial agent may be added to the wetting liquid if desired. For explanatory purposes, water is discussed as an exemplary wetting liquid.

The cooling pad may be moistened, for example, by pouring water upon the pad 100 (FIG. 1) or sleeve 500 (FIGS. 5–6), activating a water source 206 (FIG. 2), or circulating water through liquid flow passages 303, 405 internally provided in a cooling mattress 300, 400 (FIGS. 3, 4). Alternatively, the cooling pad may be pre-moistened by soaking the pad, running water over the pad, utilizing liquid flow passages, immersing the pad, etc. In this case, step 804 is performed before step 802. The use of internal liquid flow passages is most beneficial in larger foam structures, where manual wetting may not reach all areas of the foam structure.

After step 804, air flow begins in step 806. This is performed by starting a fan or other air blower. Input air may be room air, filtered air, heated or cooled air, or dehumidified air, depending upon the cooling requirements of the specific application. Air flows into the inlet 110, continues through the internal air flow passage(s), and ultimately exits from the outlet 111. As air passes through the moist foam structure, it encourages evaporation of water from the wetted foam, and therefore cools the foam structure. And because the foam structure thermally contacts the person's skin, the cooled structure cools the person's skin by conduction. And, depending upon whether the foam structure is covered with a sealant or not, the structure may also employ evaporative cooling if water is permitted to seep from the foam structure onto the person's skin and subsequently evaporate.

In the case of the cooling mattress 300, cooling may be enhanced by permitting water to seep from the absorbent layer 305 into the cushion layer 304. Namely, wetting of the cushion layer 304 causes increased evaporative cooling by placing the flowing air (in the manifold 302) in proximity to a moist region of greater volume.

Next, the operator decides whether to stop the procedure (step 808). If the cooling operation is not finished yet, cooling continues in step 810. At this point, the operator may re-moisten the cooling field as needed to sustain evaporative cooling of the foam structure. Otherwise, when cooling is done, step 808 proceeds to step 812, where the operator removes the pad 100. Then, the routine ends in step 814. At this point, the operator may dispose of the pad 100. Alternatively, the sealant on the person-receiving surface may be removed and replaced with a new or sanitized cover for convenient reuse of the cooling structure.

Other Embodiments

While the foregoing disclosure shows a number of illustrative embodiments of the invention, it will be apparent to those skilled in the art that various changes and modifications can be made herein without departing from the scope of the invention as defined by the appended claims. Furthermore, although elements of the invention may be described or claimed in the singular, the plural is contemplated unless limitation to the singular is explicitly stated. Additionally, although the present disclosure is described in the context of human persons, the invention additionally contemplates application of cooling techniques described herein to animals and other warm blooded animals. Moreover, ordinarily skilled artisans will recognize that operational sequences must be set forth in some specific order for the purpose of explanation and claiming, but the present invention contemplates various changes beyond such specific order.

What is claimed is:

1. A method of cooling a person, comprising operations of:
   contacting skin with an open cell foam structure defining one or more internal air flow passages proceeding from at least one air inlet to at least one air outlet, the structure additionally defining one or more internal liquid flow passages separate from the air flow passages, the liquid flow passages having at least one inlet;
   wetting the foam structure by directing an evaporation liquid into one or more of the liquid flow passages via the inlet; and
   blowing air into the air flow passages.

2. The method of claim 1, the wetting operation further comprising soaking the structure in water before contacting skin.

3. The method of claim 1, the structure further including a super-absorbent layer, the wetting operation further including wetting the super-absorbent layer.

4. The method of claim 1, the structure having a person-receiving surface;

the person-receiving surface being liquid penetrable;

the contacting operation including receiving a portion of the person upon the person-receiving surface;

the operation of wetting the foam structure causing wetting of the person's skin.

5. A process for cooling a person comprising operations of:

obtaining a multi-layer evaporative cooling bed, comprising:

an open cell foam mattress layer having top and bottom surfaces and including an air manifold along the top surface;

an absorbent layer with one or more internal liquid flow passages, the absorbent layer being layered over the air manifold;

placing at least a portion of a person in contact with the absorbent layer;

wetting the absorbent layer by directing a liquid into the liquid flow passages;

the absorbent layer gradually releasing moisture into the open cell foam mattress; and directing air into the air manifold.

6. The process of claim 5, the cooling bed further including a sealant layer applied to the absorbent layer; and the operations further including, the sealant layer preventing moisture in the absorbent layer from reaching the person.

7. A multi-layer evaporative cooling bed, comprising:

an open cell foam mattress layer having top and bottom surfaces and including an air manifold along the top surface;

an absorbent layer with internal liquid flow passages, the absorbent layer being layered over the air manifold and providing an outer, person-receiving surface; and a sealant layer contacting the person-receiving surface of the absorbent layer.

8. The bed of claim 7, the sealant layer being removable from the person-receiving surface.

9. The bed of claim 7, the air manifold comprising one or more passages defined through the foam mattress layer.

10. The bed of claim 7, the air manifold comprising a layer of air permeable material interposed between the foam mattress layer and the absorbent layer.

11. The bed of claim 7, the absorbent layer comprising a super-absorbent material.

12. The bed of claim 7, further comprising:

another sealant layer contacting the bottom surface.

13. A system for cooling a person, comprising:

an open cell foam structure;

one or more air flow passages defined in the open cell foam structure proceeding from one or more air inlets to one or more air outlets;

one or more liquid flow passages defined in the open cell foam structure separate from the air flow passages, the liquid flow passages having at least one liquid inlet; and an air blower coupled to at least one of the air inlets.

14. The system of claim 13, the open cell foam structure having a person-receiving surface defining a recess that is complementarily shaped to receive a prescribed body part.

15. The system of claim 13, the internal air flow passages having a serpentine shape.

16. The system of claim 13, further comprising a water source coupled to at least one of the liquid inlets.

17. The system of claim 13, further including a layer of super absorbent material contacting the open cell foam structure.

18. The system of claim 13, wherein the open cell foam structure includes open cell foam for being saturated with liquid.

* * * * *